(12) United States Patent
Anneaux et al.

(10) Patent No.: US 8,257,640 B2
(45) Date of Patent: Sep. 4, 2012

(54) MULTILAYERED COMPOSITE STRUCTURE WITH ELECTROSPUN LAYER

(75) Inventors: Bruce L. Anneaux, Lexington, SC (US); Robert L. Ballard, Orangeburg, SC (US); David P. Garner, Lexington, SC (US)

(73) Assignee: Zeus Industrial Products, Inc., Orangeburg, SC (US)

( * ) Notice: Subject to any disclaimer, the term of this patent is extended or adjusted under 35 U.S.C. 154(b) by 114 days.

(21) Appl. No.: 12/852,989

(22) Filed: Aug. 9, 2010

(65) Prior Publication Data

US 2011/0031656 A1 Feb. 10, 2011

Related U.S. Application Data

(60) Provisional application No. 61/232,252, filed on Aug. 7, 2009.

(51) Int. Cl.
*B29C 47/06* (2006.01)
*B29C 70/28* (2006.01)
*B29C 71/02* (2006.01)
*D06M 10/00* (2006.01)
*H05B 7/00* (2006.01)

(52) U.S. Cl. ........ 264/465; 264/236; 264/250; 264/255; 264/257; 264/258

(58) Field of Classification Search .................. 264/236, 264/250, 255, 257, 258, 464, 465, 466, 484
See application file for complete search history.

(56) References Cited

U.S. PATENT DOCUMENTS

| | | | |
|---|---|---|---|
| 2,158,416 | A | 5/1939 | Formhals |
| 4,043,331 | A | 8/1977 | Martin et al. |
| 4,044,404 | A | 8/1977 | Martin et al. |
| 4,127,706 | A | 11/1978 | Martin et al. |
| 4,143,196 | A | 3/1979 | Simm et al. |
| 4,287,139 | A | 9/1981 | Guignard |
| 4,323,525 | A | 4/1982 | Bornat |
| 4,432,916 | A | 2/1984 | Logan |
| 4,689,186 | A | 8/1987 | Bornat |
| 5,507,770 | A | 4/1996 | Turk |
| 5,562,986 | A | 10/1996 | Yamamoto et al. |
| 5,806,633 | A | 9/1998 | Macuga |
| 5,824,046 | A | 10/1998 | Smith et al. |

(Continued)

FOREIGN PATENT DOCUMENTS

GB 2015118 9/1979

(Continued)

OTHER PUBLICATIONS

International Search Report (PCT/US2010/044874)—2 pages, Oct. 7, 2010.

(Continued)

*Primary Examiner* — Leo B Tentoni
(74) *Attorney, Agent, or Firm* — Womble Carlyle Sandridge & Rice LLP

(57) ABSTRACT

In accordance with certain embodiments of the present disclosure, a process for forming a multilayered electrospun composite is provided. The process includes forming a dispersion of polymeric particles, a fiberizing polymer, and a solvent, the dispersion having a viscosity of at least about 50,000 cPs. Nanofibers from the dispersion are electrospun onto a first ePTFE layer. A second ePTFE layer is applied onto the nanofibers to form a composite structure. The composite structure is heated.

21 Claims, 2 Drawing Sheets

U.S. PATENT DOCUMENTS

| | | | |
|---|---|---|---|
| 5,874,165 A | 2/1999 | Drumheller | |
| 5,912,077 A | 6/1999 | Tamaru et al. | |
| 5,993,489 A | 11/1999 | Lewis et al. | |
| 6,001,125 A * | 12/1999 | Golds et al. | 623/23.7 |
| 6,124,523 A | 9/2000 | Banas et al. | |
| 6,133,165 A | 10/2000 | Tamaru et al. | |
| 6,214,039 B1 | 4/2001 | Banas et al. | |
| 6,264,684 B1 | 7/2001 | Banas et al. | |
| 6,265,333 B1 | 7/2001 | Dzenis et al. | |
| 6,270,523 B1 | 8/2001 | Herweck et al. | |
| 6,312,462 B1 | 11/2001 | McDermott et al. | |
| 6,383,214 B1 | 5/2002 | Banas et al. | |
| 6,402,779 B1 | 6/2002 | Colone et al. | |
| 6,416,896 B1 | 7/2002 | Tamaru et al. | |
| 6,436,135 B1 | 8/2002 | Goldfarb | |
| 6,505,654 B1 | 1/2003 | Andersen et al. | |
| 6,524,334 B1 | 2/2003 | Thompson | |
| 6,547,814 B2 | 4/2003 | Edwin et al. | |
| 6,579,314 B1 | 6/2003 | Lombardi et al. | |
| 6,592,614 B2 | 7/2003 | Lenker et al. | |
| 6,641,773 B2 | 11/2003 | Kleinmeyer et al. | |
| 6,673,105 B1 | 1/2004 | Chen | |
| 6,699,276 B2 | 3/2004 | Sogard et al. | |
| 6,709,455 B1 | 3/2004 | Chouinard | |
| 6,740,115 B2 | 5/2004 | Lombardi et al. | |
| 6,743,273 B2 | 6/2004 | Chung et al. | |
| 6,752,826 B2 | 6/2004 | Holloway et al. | |
| 6,770,087 B2 | 8/2004 | Layne et al. | |
| 6,790,225 B1 | 9/2004 | Shannon et al. | |
| 6,797,217 B2 | 9/2004 | McCrea et al. | |
| 6,808,533 B1 | 10/2004 | Goodwin et al. | |
| 6,827,737 B2 | 12/2004 | Hill et al. | |
| 6,833,153 B1 | 12/2004 | Roorda et al. | |
| 6,899,727 B2 | 5/2005 | Armstrong et al. | |
| 6,939,372 B2 | 9/2005 | Dong | |
| 6,949,119 B2 | 9/2005 | Myers | |
| 6,974,474 B2 | 12/2005 | Pavenik et al. | |
| 7,083,640 B2 | 8/2006 | Lombardi et al. | |
| 7,083,697 B2 | 8/2006 | Dao et al. | |
| 7,108,912 B2 | 9/2006 | Huang et al. | |
| 7,118,592 B1 | 10/2006 | Dang et al. | |
| 7,186,263 B2 | 3/2007 | Golds et al. | |
| 7,220,276 B1 | 5/2007 | Williams et al. | |
| 7,244,271 B2 | 7/2007 | Lentz et al. | |
| 7,285,132 B2 | 10/2007 | Tseng et al. | |
| 7,354,449 B2 | 4/2008 | Goodwin et al. | |
| 7,452,371 B2 | 11/2008 | Pavenik et al. | |
| 7,468,071 B2 | 12/2008 | Edwin et al. | |
| 7,510,571 B2 | 3/2009 | Spiridigliozzi et al. | |
| 7,520,894 B2 | 4/2009 | Pavenik et al. | |
| 7,550,004 B2 | 6/2009 | Bahler et al. | |
| 7,560,006 B2 | 7/2009 | Rakos et al. | |
| 7,597,710 B2 | 10/2009 | Obermiller | |
| 7,641,681 B2 | 1/2010 | Sherry et al. | |
| 7,659,219 B2 | 2/2010 | Biran et al. | |
| 7,691,141 B2 | 4/2010 | Lewis et al. | |
| 8,178,030 B2 | 5/2012 | Anneaux et al. | |
| 2001/0000188 A1 | 4/2001 | Lenker et al. | |
| 2001/0010012 A1 | 7/2001 | Edwin et al. | |
| 2001/0020181 A1 | 9/2001 | Layne | |
| 2001/0021870 A1 | 9/2001 | Edwin et al. | |
| 2001/0032008 A1 | 10/2001 | Wang et al. | |
| 2002/0026231 A1 | 2/2002 | Shannon et al. | |
| 2002/0045931 A1 | 4/2002 | Sogard et al. | |
| 2002/0111667 A1 | 8/2002 | Girton et al. | |
| 2002/0111668 A1 | 8/2002 | Smith | |
| 2002/0192468 A1 | 12/2002 | Choi | |
| 2003/0006528 A1 | 1/2003 | Edwin et al. | |
| 2003/0100944 A1 | 5/2003 | Laksin et al. | |
| 2003/0158598 A1 | 8/2003 | Ashton et al. | |
| 2003/0191522 A1 | 10/2003 | Myers | |
| 2003/0204241 A1 | 10/2003 | Dong | |
| 2003/0209835 A1 | 11/2003 | Chun et al. | |
| 2004/0033364 A1 | 2/2004 | Spiridigliozzi et al. | |
| 2004/0054397 A1 | 3/2004 | Smith et al. | |
| 2004/0093070 A1 | 5/2004 | Hojeibanet et al. | |
| 2004/0110439 A1 | 6/2004 | Chalkof et al. | |
| 2004/0167606 A1 | 8/2004 | Chouinard | |
| 2004/0236402 A1 | 11/2004 | Layne et al. | |
| 2005/0004653 A1 | 1/2005 | Gerberding et al. | |
| 2005/0025974 A1 | 2/2005 | Lennhoff | |
| 2005/0113868 A1 | 5/2005 | Devellian et al. | |
| 2005/0113909 A1 | 5/2005 | Shannon et al. | |
| 2005/0131519 A1 | 6/2005 | Hartley | |
| 2005/0154448 A1 | 7/2005 | Cully et al. | |
| 2005/0283224 A1 | 12/2005 | King | |
| 2005/0288767 A1 | 12/2005 | Kujawski et al. | |
| 2006/0015171 A1 | 1/2006 | Armstrong | |
| 2006/0020328 A1 | 1/2006 | Tan | |
| 2006/0074482 A1 | 4/2006 | Lewis et al. | |
| 2006/0259133 A1 | 11/2006 | Sowinski et al. | |
| 2006/0266474 A1 | 11/2006 | Burnside et al. | |
| 2007/0191936 A1 | 8/2007 | Williams et al. | |
| 2007/0207186 A1 | 9/2007 | Scanlon et al. | |
| 2007/0208410 A1 | 9/2007 | Berra et al. | |
| 2007/0244539 A1 | 10/2007 | Lentz et al. | |
| 2008/0009781 A1 | 1/2008 | Anwar et al. | |
| 2008/0033522 A1 | 2/2008 | Grewe et al. | |
| 2008/0143012 A1 * | 6/2008 | Norvell et al. | 264/175 |
| 2008/0161907 A1 | 7/2008 | Chen et al. | |
| 2008/0167708 A1 | 7/2008 | Molland et al. | |
| 2008/0254091 A1 | 10/2008 | Lee et al. | |
| 2008/0296808 A1 * | 12/2008 | Joo et al. | 264/465 |
| 2009/0076587 A1 | 3/2009 | Cully et al. | |
| 2009/0125092 A1 | 5/2009 | McCrea et al. | |
| 2009/0157173 A1 | 6/2009 | Bjork, Jr. | |
| 2009/0163994 A1 | 6/2009 | Quigley et al. | |
| 2009/0187240 A1 | 7/2009 | Clerc et al. | |
| 2009/0192627 A1 | 7/2009 | Shin et al. | |
| 2009/0233057 A1 | 9/2009 | Aksay et al. | |
| 2009/0270907 A1 | 10/2009 | Todd et al. | |
| 2009/0312834 A1 | 12/2009 | Wood et al. | |
| 2010/0010515 A1 | 1/2010 | Farnsworth et al. | |
| 2010/0013126 A1 * | 1/2010 | Ishaque et al. | 264/465 |
| 2010/0074934 A1 | 3/2010 | Hunter | |
| 2010/0194000 A1 | 8/2010 | Petras et al. | |

FOREIGN PATENT DOCUMENTS

| | | |
|---|---|---|
| JP | 02-0571379 | 10/1996 |
| KR | 10-0820162 | 4/2008 |
| KR | 10-0845239 | 7/2008 |
| WO | 98/31306 | 7/1998 |
| WO | 2005/060875 | 7/2005 |
| WO | WO-2008022993 A2 * | 2/2008 |

OTHER PUBLICATIONS

International Search Report (PCT/US2010/044879)—2 pages, Sep. 24, 2010.

Kim et al., "Structural Studies of Electrospun Cellulose Nanofibers," *Polymer*, 2006, pp. 5097-5107, vol. 47.

PCT International Search Report from PCT/US10/024246, dated Aug. 16, 2010.

Written Opinion of the International Searching Authority, PCT/US10/024246, dated Aug. 16, 2010.

* cited by examiner

MULTILAYERED COMPOSITE STRUCTURE WITH ELECTROSPUN LAYER

CROSS-REFERENCE TO RELATED APPLICATION

The present application is based on and claims priority to U.S. Provisional Application Ser. No. 61/232,252 having a filing date of Aug. 7, 2009, which is incorporated by reference herein.

BACKGROUND

Electrostatic spinning of polytetrafluoroethylene (PTFE) into continuous fiber allows for the formation of non-woven sheets, tubes, and coatings with potential for multiple other applications and forms. The process of electrostatic spinning is well known in the literature and the patenture as represented by U.S. Pat. Nos. 2,158,416; 4,432,916; 4,287,139; 4,143,196; 4,043,331; 4,689,186 and 6,641,773 each of which is incorporated herein by reference thereto. While most of these patents pertain to soluble polymers or thermoplastics, none pertain directly to the formation of fibers or mat from virtually insoluble polymers or those that do not flow readily on heating to elevated temperatures. A review of the literature and patenture revealed limited reference to the process whereby a polymer that meets the properties of limited solubility and inability to readily flow upon heating such as PTFE can be formed into a fiber suitable for electrostatic spinning into various structures. U.S. Pat. Nos. 4,323,525 and 4,044,404, both of which are incorporated herein by reference, provide information related to processing and electrostatic spinning of PTFE from an aqueous or other dispersion.

However, such conventional processes have several shortcomings. Such processes describe the use of low viscosity PTFE dispersions (15,000 cPs) which do not result in uniform or consistent fiber formation. Furthermore, such processes describe the use of a grounded spinning head and a charged target. Observation shows various levels of degradation in samples produced by reverse polarity. Conventional processes also fail to accommodate for shrinkage of a mat during sintering.

Thus, a need exists for processes that address the deficiencies described above. Materials made from such processes would also be particularly beneficial.

SUMMARY

In accordance with certain embodiments of the present disclosure, a process for forming a multilayered electrospun composite is provided. The process includes forming a dispersion of polymeric particles, a fiberizing polymer, and a solvent, the dispersion having a viscosity of at least about 50,000 cPs. Nanofibers from the dispersion are electrospun onto a first ePTFE layer. A second ePTFE layer is applied onto the nanofibers to form a composite structure. The composite structure is heated.

In other embodiments of the present disclosure, a process for forming a multilayered electrospun composite structure is disclosed. The process includes electrospinning a dispersion having a viscosity of at least about 50,000 cPs and comprising polymeric particles, a fiberizing polymer, and a solvent, onto a first side of an ePTFE layer. The process further includes electrospinning a dispersion having a viscosity of at least about 50,000 cPs and comprising polymeric particles, a fiberizing polymer, and a solvent, onto a second side of the ePTFE layer to form a composite structure. The composite structure is heated.

In still other embodiments of the present disclosure, a process for forming a multilayered electrospun composite structure is described. The process includes forming a dispersion of polymeric particles, a fiberizing polymer, and a solvent, the dispersion having a viscosity of at least about 50,000 cPs. Nanofibers from the dispersion are electrospun onto a first ePTFE layer. A substrate is applied onto the nanofibers to form a composite structure. The composite structure is heated.

Through diligent research the inventors have determined that electrospun materials, such as PTFE, when applied to ePTFE membranes constitutes an additional application, form, and use of electrospun materials. Furthermore, the inventors have determined that a wide range of electrospun materials when combined in layers with ePTFE membranes and/or other substrates can create composite membrane structures with new and unique properties.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present invention is related to multilayered composites comprising one or more electrospun (also referred to herein as "espin" and/or "espun" and/or "espinning") membranes attached to one or more expanded polytetrafluoroethylene (also referred to herein as "ePTFE") membranes. In certain embodiments, the espin membranes can include polytetrafluoroethylene (also referred to herein as "espin PTFE"), however, many other suitable materials can be espun and used in addition to or in combination with such espin PTFE. For example, other suitable materials that can be espun in accordance with the present disclosure include nylons, polyurethanes (PU), polyesters, fluorinated ethylene propylene (FEP), or the like. Polymers that can be placed in a solution have the potential to be espun. Polymer particles that can be made into dispersions (such as, PTFE, FEP, and the like) also have the potential to be espun. The dispersions (espun PTFE)

must be sintered to develop the desired properties, but many polymers espun from solution develop their properties during spinning and drying. The attachment of the espin layer(s) can occur during sintering.

For example, in certain embodiments the high molecular weight of the polytetrafluoroethylene that is present in the espin PTFE layer and the ePTFE layer melts at the sintering temperatures, but does not flow. Thus, PTFE present in each of the layers has an opportunity to form physical bonding between adjacent layers. Compression of the layers to force more intimate contact is advantageous. The multi-layered composite is particularly useful in medical, industrial, filtration, military and consumer applications.

A particularly preferred ePTFE is an air permeable expanded membrane. A membrane which is exemplary for demonstrating the invention is described in U.S. Pat. No. 4,902,423 which is incorporated herein by reference. Another exemplary membrane is described in U.S. Pat. No. 3,962,152 which is incorporated herein by reference.

Numerous configurations are contemplated in accordance with the present disclosure. For instance, the construction can be a two layer or multiple layer composite of the materials described herein.

Figure 1:
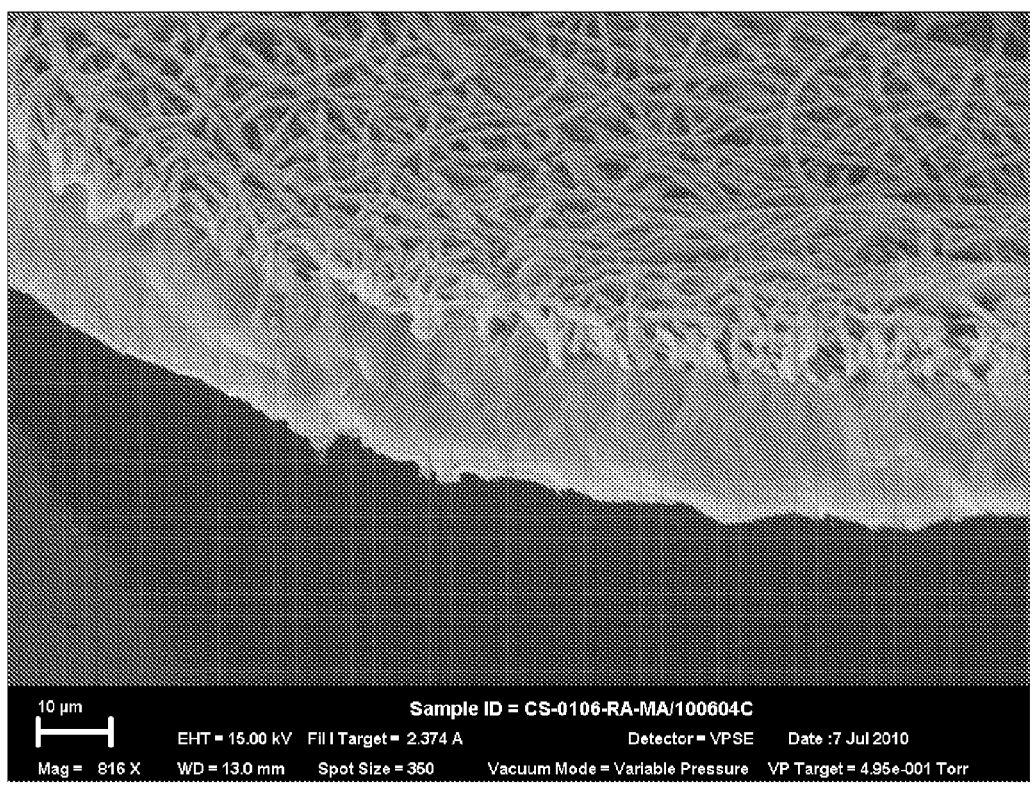
FIG. 1 illustrates an SEM image of a multilayered composite construction in accordance with the present disclosure.
Figure 2:
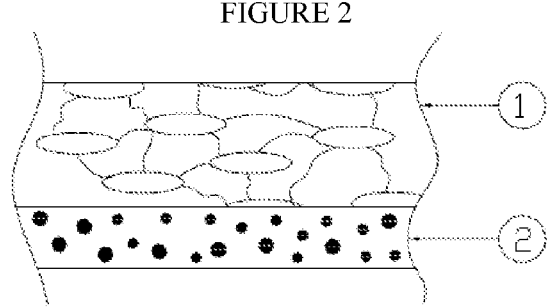
FIGS. 2-5 illustrate cross-sectional views of different multilayered composites in accordance with the present disclosure.

Referring to FIG. 2, a cross-section of a multilayer composite in accordance with the present disclosure is illustrated. The composite includes an ePTFE layer 1 and an espin layer 2. FIG. 1 illustrates an SEM image of such a multilayered composite in which the espin layer is espin PTFE. Advantages of such a configuration include an asymmetrical flow structure because pore size can be controlled. In addition, the presence of the espin material can result in improved adhesion of the composite to subsequent layers. Importantly, the espin material can also result in modification of the ePTFE surface properties.

Figure 3:
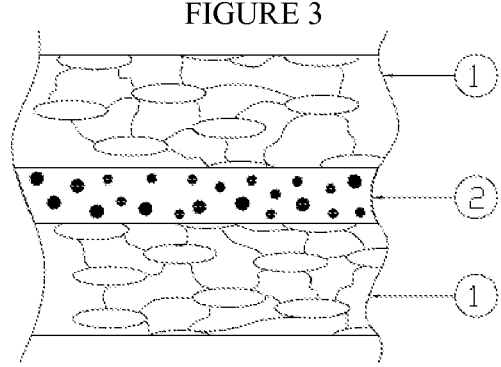

Turning to FIG. 3, another cross-section of a multilayer composite in accordance with the present disclosure is illustrated. The composite includes an ePTFE layer 1, an espin layer 2, and an ePTFE layer 1. The espin layer 2 is sandwiched between the ePTFE layers 1. Such a configuration allows the mechanical properties of the composite to be modified, as desired. For example, material recovery can be improved after compression. The espin material selection can be adjusted to improve bonding properties between layers. In this regard, any espun material that has adhesive potential can act to bond layers together. Espun PTFE can act to bond the ePTFE layers together. Espun PU can also bond ePTFE layers together. In certain embodiments, espun PTFE must be heated to 385° C. to develop bonding characteristics while materials such as PU can create a bonding situation at much lower temperatures.

Figure 4:
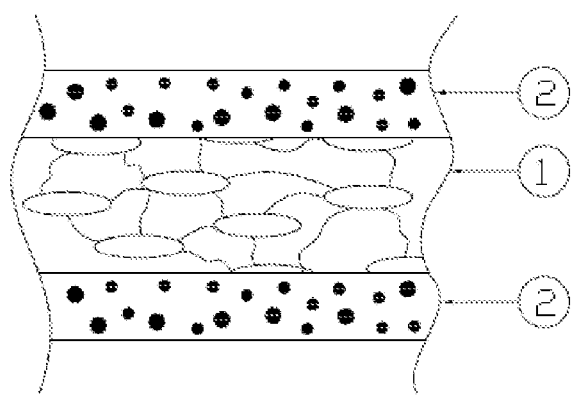

In yet another embodiment of the present disclosure, a cross-sectional view of an espin layer 2, an ePTFE layer 1, and an espin layer 2 are illustrated as FIG. 4. The ePTFE layer 1 is sandwiched between the espin layers 2. Advantages of such a construction include modulation of surface properties through the espin layer including a) better adhesion to the composite construction if desired, b) changing the surface functionality of the composite, c) manipulation of cellular in-growth and response, and d) increased porosity for improved ingress of other materials.

Figure 5:
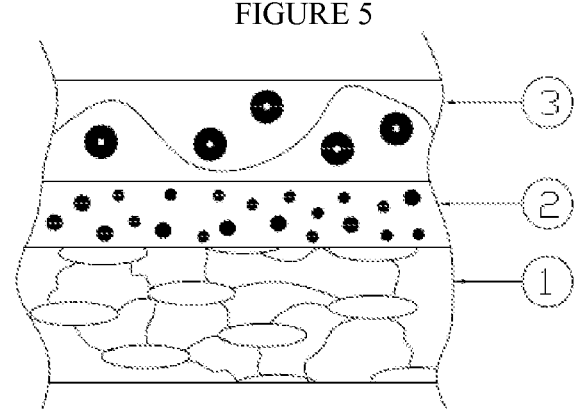

FIG. 5 illustrates yet another embodiment of a cross-section of a multilayer composite construction in accordance with the present disclosure. The composite includes a substrate layer 3, an espin layer 2, and an ePTFE layer 1. The substrate layer can include woven and nonwoven fabrics of natural or man-made fibers, plastic or ceramic membranes, metal, ceramic, and plastic meshes, or the like. For instance, metal stents are a type of metal mesh. Such a construction allows for a structure which has increased robustness and durability, while maintaining porosity, air permeability and other desired properties of porous materials. The composite can be thermally or adhesively bonded to other woven or nonwoven porous substrates. Such a composite also results in improved pore size distribution and improved durability, which can be very beneficial in filtration applications where debris and particulate are contacting the media surface at high velocities. In addition, the overall filtration efficiency can be improved as a result of the microstructure of the espin fiber entanglement.

The electrospun layer is preferably applied directly to the membrane through electrospinning methods understood by those skilled in the art; however, it could also be applied using mechanical nips or lamination as well. These latter techniques include pressing an electrospun layer onto a second material layer and heating to a complimentary temperature. The pressing technique may use a flat press or mechanical nip roller.

The properties and characteristics are a compilation of both a non-woven and a membrane. The composite can be prepared with controlled fiber, node and fibril sizes and manipulated mechanical values such as bond strength, elongation properties and tensile strengths.

The properties and characteristics of the composite can be a compilation of the individual properties of the substrate layer, espin layer, and the ePTFE layers. The composite can be prepared with controlled fiber, node and fibril sizes and manipulated mechanically, such as to improve bond strength, elongation properties and tensile strengths, in the final composite.

Typical construction of multiple layers may produce thickness ranging from about 0.0001 inches to about 0.25 inches overall thicknesses at widths of about 0.032 inches to about 80 inches. The individual layers can have a thickness that varies from about 0.0001 inches to about 0.25 inches. Final material size varies greatly as the composites can be produced as sheets or tubes at continuous roll lengths. The composite internodal distance (IND) can be about 0.1 to about 200 μm with porosity ranging from about 20 to 90%. Pore structure as defined by ASTM F316, incorporated by reference herein, can range from about 0.05 to about 50 μm. Due to the construction of the composites, the IND, pore size and porosity can vary from layer to layer, within the cross section of the composite, depending on the construction. An example would be an asymmetrical construction where pores change in size from large to small based on layer evaluations from surface to surface throughout the media.

In certain embodiments of the present disclosure, the process can require a dispersion or suspension of PTFE solids between about 10 to 85% by weight to aid in the processing of the collected fibrous mat into a form that has sufficient green strength. However, as described above, other suitable polymers can be utilized for the espin dispersion. If the solid content in the dispersion is too low, there will be no, or poor, mechanical integrity to the resulting material. Second, the selection of the polymer used to increase the viscosity of the solution, suspension or dispersion to be spun must be selected carefully.

Additionally, when sintering or bonding espin layers it is necessary to insure that temperatures are selected to properly sinter the material, such that the resulting product has good mechanical integrity.

To produce a non-woven espin PTFE material, a narrow particle size distribution PTFE powder is provided in an aqueous dispersion. The particle size would preferably be about 0.05 to 0.8μ. About 1 to 10 wt % by weight of a fiberizing polymer is added to the volume of PTFE aqueous dispersion. The fiberizing polymer should have a high solubility in water with a solubility of greater than about 0.5 wt % being preferred. It is preferable that the fiberizing polymer has an ash content of less than about 5 wt %, when sintered at about 400° C., with even lower being more preferred. Without limit thereto, particularly preferred fiberizing polymers can include dextran, alginates, chitosan, guar gum compounds, starch, polyvinylpyridine compounds, cellulosic compounds, cellulose ether, hydrolyzed polyacrylamides, polyacrylates, polycarboxylates, polyvinyl alcohol, polyethylene oxide, polyethylene glycol, polyethylene imine, polyvinylpyrrolidone, polylactic acid, polymethacrylic acid polyitaconic acid, poly 2-hydoxyelthyl acrylate, poly 2-dimethylaminoethyl methacrylate-co-acrylamide, poly n-isopropylacrylamde, poly 2-acrylamido-2-methyl-1-propanesulfonic acid, poly (methoxyethylene), poly(vinyl alcohol), poly(vinyl alcohol) 12% acetyl, poly(2,4-dimethyl-6-triazinylethylene), poly(3-morpholinylethylene), poly(N-1,2,4-triazolyethylene), poly (vinyl sulfoxide), poly(vinyl amine), poly(N-vinyl pyrrolidone-co-vinyl acetate), poly(g-glutamic acid), poly(N-propanoyliminoethylene), poly(4-amino-sulfo-aniline), poly [N-(p-sulphophenyl)amino-3-hydroxymethyl-1,4-phenyleneimino-1,4-phenylene)], isopropyl cellulose, hydroxyethyl, hydroxylpropyl cellulose, cellulose acetate, cellulose nitrate, alginic ammonium salts, i-carrageenan, N-[(3'-hydroxy-2',3'-dicarboxy)ethyl]chitosan, konjac glocomannan, pullulan, xanthan gum, poly(allyammonium chloride), poly(allyammonium phosphate), poly(diallydimethylammonium chloride), poly(benzyltrimethylammonium chloride), poly(dimethyldodecyl(2-acrylamidoethyly) ammonium bromide), poly(4-N-butylpyridiniumethylene iodine), poly(2-N-methylpridiniummethylene iodine), poly(N methylpryidinium-2,5-diylethenylene), polyethylene glycol polymers and copolymers, cellulose ethyl ether, cellulose ethyl hydroxyethyl ether, cellulose methyl hydroxyethyl ether, poly(1-glycerol methacrylate), poly(2-ethyl-2-oxazoline), poly(2-hydroxyethyl methacrylate/methacrylic acid) 90:10, poly(2-hydroxypropyl methacrylate), poly(2-methacryloxyethyltrimethylammonium bromide), poly(2-vinyl-1-methylpyridinium bromide), poly(2-vinylpyridine N-oxide), poly(2-vinylpyridine), poly(3-chloro-2-hydroxypropyl-2-methacryloxyethyldimethylammonium chloride), poly(4-vinylpyridine N-oxide), poly(4-vinylpyridine), poly (acrylamide/2-methacryloxyethyltrimethylammonium bromide) 80:20, poly(acrylamide/acrylic acid), poly(allylamine hydrochloride), poly(butadiene/maleic acid), poly(diallyldimethylammonium chloride), poly(ethyl acrylate/acrylic acid), poly(ethylene glycol)bis(2-aminoethyl), poly (ethylene glycol) monomethyl ether, poly(ethylene glycol)-bisphenol A diglycidyl ether adduct, poly(ethylene oxide-b-propylene oxide), poly(ethylene/acrylic acid) 92:8, poly(1-lysine hydrobromide), poly(1-lysine hydrobromide), poly (maleic acid), poly(n-butyl acrylate/2-methacryloxyethyltrimethylammonium bromide), poly(N-iso-propylacrylamide), poly(N-vinylpyrrolidone/2-dimethylaminoethyl methacrylate), dimethyl sulfatequaternary, poly(N-vinylpyrrolidone/vinyl acetate), poly(oxyethylene) sorbitan monolaurate (Tween 20®), poly (styrenesulfonic acid), poly(vinyl alcohol), N-methyl-4(4'-formylstyryl)pyridinium, methosulfate acetal, poly(vinyl methyl ether), poly(vinylamine) hydrochloride, poly(vinylphosphonic acid), poly(vinylsulfonic acid) sodium salt, polyaniline, and combinations thereof. Again, however, such fiberizing polymers are also contemplated for use with other polymer espin dispersions.

A particularly preferred fiberizing polymer is polyethylene oxide with a molecular weight between about 50,000 to 4,000,000 amu polyethyleneoxide. After mixing, the PTFE and fiberizing polymer dispersion is preferably allowed to homogenize. In a particularly preferred method the polymer dispersion is allowed to form slowly, without agitation, followed by transfer to a jar roller that will turn it at a constant rate for several more days. The present disclosure contemplates the use of dispersions of greater than 50,000 cPs to provide for more uniform and consistent fiber formation as well as faster builds. It is preferred to create a uniform dispersion that has little to no air trapped in the resulting highly viscous mixture. Once the dispersion is of uniform consistency it is preferably filtered to remove any clumps or gels. The filtered dispersion with the desired viscosity is then loaded, in a controlled pumping device with a fixed conductive element which acts as the charge source.

A particularly preferred conductive element is one with one or several orifices. The orifice size is preferably, but not limited to, about 0.01 to 3.0 mm in diameter. The ejection volume from the pumping device is set to a predetermined rate that is dependent on the form being made and the desired fiber diameters. The charge source is preferably connected to the positive side of a precision DC power supply. The negative side of the power supply is preferably connected to the collection surface or target. The polarity can be reversed but this is not preferred.

The surface can be a drum, device or sheet. The surface can be a metal, ceramic or polymeric material with particularly preferred materials selected from stainless steel, cobalt chrome, nickel titanium (nitinol) and magnesium alloys. The voltage on the power supply is increased to the desired voltage to uniformly draw out the polymer/PTFE dispersion.

The applied voltage is typically from about 2,000 to 80,000 volts. The charge induced by the connection of the power supply repels the charged polymer away from the charge source and attracts them to the collection surface.

The collection target is preferably placed perpendicular to the pump and orifice system and is moved in at least one direction such that the entire surface is uniformly covered, with the fibers drawn towards the target. Once the collection surface has been adequately covered the material is preferably cured, sintered, and dried (which can occur simultaneously or in a series of steps), either in place, by placing the entire collection surface in an oven, or by removing the sheet tube or other form from the collection surface and sintering it in an oven.

It is well known to those skilled in the art that espin fabrics undergo shrinkage upon sintering. While not limited to any theory the shrinkage is believe to occur in two steps. Initially, the fibers and fabrics as spun contain both water and a fiberizing polymer as previously described. Upon completion of spinning the samples dry and undergo a small degree of fiber rearrangement. At a later time the samples are heated by exposing the fibers and fabrics to temperatures of about 35° C. to about 485° C. for a period of time.

To accommodate for shrinkage, the fiber and fabrics can be spun onto an expanded structure. The structure can then be removed or contracted. During sintering of the espin layer, the fabric shrinks to a smaller size without cracking. Another method involves spinning the fibers and fabrics onto a structure which can then be expanded and/or contracted prior to or during sintering. The range of contraction or expansion and contraction is on the order of about 3 to 100% and depends upon the thickness and size of the electrodeposited fabric. Alternatively the espin layer can be placed upon a surface which also contracts during sintering.

For a sheet of fabric, if the direction of the deposition is given as the perpendicular to the plane of the fabric then contraction or expansion/contraction must occur in at least one or more of the directions in the plane of the fabric. For a fabric deposited upon a cylindrical surface the fabric must be contracted or contracted/expanded radially and/or longitudinally. For a spherical surface the fabric must be contracted or contracted/expanded radially. These basic concepts of contraction and/or expansion/contraction can be applied to any electrospun fabric independent to the shape of the surface upon which it was spun. Thus, very complex fabric shapes based upon espin fabric become possible.

The espin layer is preferably fibrous. Particularly preferred espin fibers have a diameter of at least 0.1μ. In a particularly preferred embodiment the product, after sintering, has fibers deposited in a density such there is a range of distances of 0.1 to 50μ between points of contact.

The present disclosure can be better understood with reference to the following examples.

EXAMPLES

The following general guidelines are used for the processing examples described herein of various ePTFE and espin composite constructions.

1. In espin PTFE embodiments, the viscosity of the dispersion may be changed by the addition or removal of water from the dispersion without changing the PEO to PTFE ratio.
2. A radially expanded ePTFE tube or biaxial oriented sheet is placed over a round or flat base plate to form a desired geometric shape.
3. The espin polymer layer is applied at a desired thickness, typically about 0.5 to 1000 μm, onto the ePTFE or onto a surface which is then mated to the ePTFE membrane, resulting in a composite structure.
4. If the espin coating is applied wet to the ePTFE, it is allowed to dry before moving to the next process. However, if it is processed as a single espin sheet and has dried, it will be mated to the oriented porous ePTFE layer. The mating process between the materials can be repeated multiple times until a desired multilayered composite structure is created.
5. The ePTFE/espin composite is then covered with a non-sticking release foil.
6. Once the composite is positioned against a base tool, pressure is applied to the surface of the foil, thereby aiding the bonding process.
7. The composite construction is placed in an oven at temperatures of about 35° C. to about 485° C. to allow all materials to bond together. The bonding temperature selection is based on material selection.
8. Once the part is removed from the oven and cooled at a rate of about 15 to 25 degrees per minute, it is uncovered and tested for specified properties.

Example 1

Type I Construction: ePTFE/espin PTFE:

An 80μ thick stainless steel (SS) sheet 46 cm×36 cm was wrapped around a rotating drum. The drum assembly was placed into a rotating chuck such that it was positioned to allow espinning along the entire length of the turning drum assembly.

An approximately 80,500 cPs espinning dispersion based on a mixture of 4.2% (PEO/PTFE), 300,000 amu polyethylene oxide and Daikin D210 60% PTFE dispersion which had been allowed to homogenize and then turned and filtered to achieve a smooth consistency was placed into a 10 ml plastic syringe fitted with a 21 gauge needle. The syringe was placed into a KD Scientific Model 780200L syringe pump and set to a 0.5 ml/hour pumping rate. The needle tip was positioned at approximately 13 cm from the rotating drum assembly. The rotation of the drum assembly was approximately 30 rpm. A traverse was used to move the espinning needle along the length of the drum with a rate of travel of 3.0 mm/sec. The return points for the traverse were set at the ends of the SS sheet. A voltage of 10.0 kV was employed. PTFE was electrospun onto the drum for 60 minutes under these conditions to yield an approximately 40μ (as deposited post sintering) thick covering of PTFE fibers. The sheet containing the PTFE membrane was removed from the drum and dried overnight.

A biaxially (Biax) expanded approximately 35 cm×40 cm ePTFE sheet with an intermodal distance (IND) of 10-30μ, thickness of 34μ, and bubble point<3μ was placed over and centered onto a 46 cm×36 cm stainless steel sheet.

The SS sheet holding the dried espin PTFE membrane was then directly positioned over the SS sheet holding the ePTFE membrane and the two sheets brought together such that the ePTFE and espin PTFE membranes were in intimate contact. The SS foil/ePTFE/espin PTFE/SS foil structure was then wrapped onto a 3μ ID stainless steel tube to create the assembly. The entire assembly was then wrapped in unsintered 40μ thick ePTFE membrane with 5 wraps tightly applied around the entire assembly. This was then placed in an oven at 385° C. for 15.5 minutes. Sintering temperature and time may vary depending on the composite's thickness and basis weight. After sintering, the assembly was removed from the oven and placed in a cooling air box to cool for 30-60 minutes. After cooling, the ePTFE membrane was unwrapped and a 22 cm×28 cm portion was removed from the center of the espin/ePTFE composite.

Examples 2-6

Type I Construction: ePTFE/espin PTFE:

Examples 2-6 were made similarly with the modifications from Example 1 and are shown in Table I. In general, the major predictor of the Mean Pore Size Diameter is the ePTFE membrane IND. However, the pore size is also affected by the pressure applied on the composite during sintering as shown by comparison of the composite thicknesses of Examples 1 and 4 with greater pressure yielding a smaller pore size. The thickness of the espin PTFE layer also has an effect as shown by Examples 1, 2, and 3 with greater thickness yielding a smaller pore size.

Example 7

Type I Construction: ePTFE/espin Polyurethane (PU)

A biaxially (Biax) expanded approximately 35 cm×40 cm ePTFE sheet with an intermodal distance (IND) of 10-30μ, thickness of 34μ, and bubble point<3μ was placed over and centered onto a 46 cm×36 cm stainless steel sheet.

An approximately 500 cPs espinning solution based on a mixture of Chronoflex AR (AdvanSource Biomaterials) (PU) 11% in a mixture of 37.5% acetone and 62.5% Dimethylacetamide was placed into a 10 ml plastic syringe fitted with a 21 gauge needle. The syringe was placed into a KD Scientific Model 780200L syringe pump and set to a 0.35 ml/hour pumping rate. The needle tip was positioned at approximately 13 cm from the rotating drum assembly. The rotation of the drum assembly was approximately 30 rpm. A traverse was used to move the espinning needle along the length of the drum with a rate of travel of 3.0 mm/sec. The return points for the traverse were set at the ends of the SS sheet. A voltage of 9.2 kV was employed. PTFE was electrospun onto the drum for 240 minutes under these conditions to yield an approximately 2μ thick covering of PU fibers. The sheet containing the PTFE/PU composite membrane was removed from the drum and dried overnight.

Example 8

Type I Construction: ePTFE/espin Polyurethane (PU):

Example 8 was made similarly with the modifications from Example 7 shown in Table II. Again a thicker layer of the espin PU resulted in decreased pore size.

Example 9

Type II Construction: ePTFE/espin PTFE/ePTFE:

A biaxially (Biax) expanded approximately 10 cm long ePTFE tube with an intermodal distance (IND) of 30μ, internal diameter (ID) of 4 mm, wall thickness (WT) of 0.4 mm, and porosity of 80.33% was stretched over and centered along a 10 mm exterior diameter (OD) aluminum rod of 35 cm length. The tube assembly was placed into a rotating chuck such that it was positioned to allow espinning along the entire length of the turning tube assembly.

An approximately 94,000 cPs espinning dispersion based on a mixture of 4.2% (PEO/PTFE), 300,000 amu polyethylene oxide and Daikin D210 60% PTFE dispersion which had been allowed to homogenize and then turned and filtered to achieve a smooth consistency was placed into a 10 ml plastic syringe fitted with a 16 gauge needle. The syringe was placed into a Harvard Model 702100 syringe pump and set to a 0.5 ml/hour pumping rate. The needle tip was positioned at approximately 13 cm from the rotating tube assembly. The rotation of the tube assembly was approximately 60 rpm. A traverse was used to move the espinning needle along the length of the tube with a rate of travel of 2.5 mm/sec. The return points for the traverse were set at the ends of the Biax tube. A voltage of 9.3 kV was employed. PTFE was electrospun onto the tube for 30 minutes under these conditions to yield an approximately 20μ (as deposited post sintering) thick covering of PTFE fibers.

After allowing the tube assembly to dry overnight an ePTFE membrane of basis weight 8.426 g/m2 and thickness of 30μ was wrapped 6 times around the tube assembly. The tube assembly was then wrapped in 80μ thick stainless steel foil followed by being further wrapped 5 times with unsintered 40μ thick ePTFE membrane applied tightly around the entire assembly. The tube assembly was then placed into an oven preheated to 385° C. for 4.0 minutes. After removal from oven, cooling, and unwrapping the composite tube was determined to have a thickness of 0.149 mm.

Examples 10-15

Type II Construction: ePTFE/espin PTFE/ePTFE:

Examples 10-15 were made similarly with the particulars of each Example shown in Table III.

Example 16

Type III Construction: espin PTFE/ePTFE/espin PTFE:

A 40μ thick aluminum foil sheet 46 cm×6.2 cm was wrapped around a rotating drum. The drum assembly was placed into a rotating chuck such that it was positioned to allow espinning along the entire length of the turning drum assembly.

An espinning dispersion based on a mixture of 5.2% (PEO/PTFE) 300,000 amu polyethylene oxide and Daikin D210, 60% PTFE dispersion which had been allowed to homogenize and then turned and filtered to achieve a smooth consistency was placed into a 10 ml plastic syringe fitted with a 16 gauge needle. The syringe was placed into a KD Scientific Model 780200L syringe pump and set to a 0.09 ml/hour pumping rate. The needle tip was positioned at approximately 20 cm from the rotating drum assembly. The rotation of the drum assembly was approximately 30 rpm. A traverse was used to move the espinning needle along the length of the drum with a rate of travel of 3.0 mm/sec. The return points for the traverse were set at the ends of the aluminum foil. A voltage of 18.0 kV was employed. PTFE was electrospun onto the drum for 30 minutes under these conditions to yield an approximately 80μ (as deposited post sintering) thick covering of PTFE fibers. The aluminum foil containing the PTFE membrane was removed from the drum and dried.

After drying the green strength of the composite allowed the removal of the PTFE membrane from the foil and placement, centering, and loose wrapping of a 10 cm×6.5 cm portion of the PTFE membrane around a 1.0 cm exterior diameter (OD) aluminum tube twice. An ePTFE membrane: thickness—130μ, IND—12.45μ, and porosity of—51% was then wrapped 3 times around the espin PTFE to create a tube/espin PTFE/ePTFE assembly. The tube assembly was placed into a rotating chuck such that it was positioned to allow espinning along the entire length of the turning tube assembly.

An espinning dispersion based on a mixture of 5.2% (PEO/PTFE) 300,000 amu polyethylene oxide and Daikin D210, 60% PTFE dispersion which had been allowed to homogenize and then turned and filtered to achieve a smooth consistency was placed into a 10 ml plastic syringe fitted with a 16 gauge needle. The syringe was placed into a KD Scientific Model 780200L syringe pump and set to a 0.05 ml/hour pumping rate. The needle tip was positioned at approximately 11.5 cm from the rotating tube assembly. The rotation of the tube assembly was approximately 30 rpm. A traverse was used to move the espinning needle along the length of the tube with a rate of travel of 3.0 mm/sec. The return points for the traverse were set at the ends of the espin PTFE/ePTFE assembly. A voltage of 16.0 kV was employed. PTFE was electrospun onto the assembly for 15 minutes under these conditions to yield an approximately 60μ (as deposited post sintering) thick covering of PTFE fibers. The assembly was removed from the drum, dried, and placed onto a fixture. The assembly was then placed upright into an oven preheated to 385° C. for 4.0 minutes.

Example 17

Type IV Construction: Substrate/espin PTFE/ePTFE:

A 40μ thick non stick aluminum foil sheet 43 cm×38 cm was wrapped around a rotating drum. An approximately 35 cm×30 cm ePTFE sheet with a basis weight of 4.997 gsm, thickness of 7μ, and porosity of 72% was placed over, centered, and affixed onto the aluminum foil. The drum assembly was placed into a rotating chuck such that it was positioned to allow espinning along the entire length of the turning drum assembly.

An approximately 163,000 cPs espinning dispersion based on a mixture of 4.2% (PEO/PTFE), 300,000 amu polyethylene oxide and Daikin D210 60% PTFE dispersion which had been allowed to homogenize and then turned and filtered to achieve a smooth consistency was placed into two 10 ml plastic syringes fitted with 16 gauge needles. The syringes were placed into a KD Scientific Model 780200L syringe pump and set to a 0.75 ml/hour pumping rate. The needle tips were positioned at approximately 20.3 cm from the rotating drum assembly. The rotation of the drum assembly was approximately 30 rpm. A traverse was used to move the espinning needle along the length of the drum with a rate of travel of 3.0 mm/sec. The return points for the traverse were set at the ends of the ePTFE membrane sheet. A voltage of 17.5 kV was employed. PTFE was electrospun onto the drum for 30 minutes under these conditions to yield an approximately 50μ (as deposited post sintering) thick covering of PTFE fibers. The aluminum foil sheet containing the ePTFE/espin PTFE composite membrane was then removed from the drum and dried overnight. After drying the green strength was sufficient to allow the removal of the ePTFE/espin PTFE composite membrane from the foil.

A 5 cm wide section of the composite membrane was wound 3 times around a 5 cm long, 0.5 cm OD porous metal tube with the espin layer in contact with the tube. The entire assembly was then placed on a fixture, wrapped in aluminum foil and then wrapped with unsintered 40μ thick ePTFE membrane tightly applied around the entire assembly. The assembly was then placed in an oven at 385° C. for 4 mins. After cooling the composite membrane had good appearance and adherence to the metal tube.

TABLES

TABLE I

Type I: ePTFE/espin PTFE Examples

| Example | ePTFE Membrane Thickness | ePTFE Membrane IND | PTFE Dispersion Viscosity cPs | Espin PTFE Thickness | Espin PTFE/ePTFE Composite Thickness | Mean Pore Size Diameter |
|---|---|---|---|---|---|---|
| Membrane | | | | | | 1.3029μ |
| 1 | 34μ | 10-30μ | 80,500 | 40μ | 31μ | 0.5564μ |
| 2 | 34μ | 10-30μ | 80,500 | 50μ | 31μ | 0.4690μ |
| 3 | 34μ | 10-30μ | 80,500 | 80μ | 32μ | 0.4401μ |
| 4 | 34μ | 10-30μ | 87,000 | 40μ | 30μ | 0.5406μ |
| Membrane | | | | | | 0.2968μ |
| 5 | 23μ | 2-5μ | 101,000 | 20μ | 18μ | 0.2915μ |
| 6 | 23μ | 2-5μ | 105,000 | 30μ | 22μ | 0.2921μ |

TABLE II

Type I: ePTFE/espin PU Examples

| Example | ePTFE Membrane Thickness | ePTFE Membrane IND | PU Viscosity cPs | Espin PU thickness | Espin PTFE/ePTFE Composite Thickness | Mean Pore Size Diameter |
|---|---|---|---|---|---|---|
| Membrane | | | | | | 0.2968μ |
| 7 | 23μ | 2-5μ | 500 | 2μ | 25μ | 0.2809μ |
| 8 | 23μ | 2-5μ | 500 | 1μ | 24μ | 0.2930μ |

TABLE III

Type II: ePTFE/espin PTFE/ePTFE Examples

| Example | 9 | 10 | 11 | 12 | 13 | 14 | 15 |
|---|---|---|---|---|---|---|---|
| Rod Diameter | 10 mm | 12 mm | 20 mm | 20 mm | 20 mm | 20 mm | 26 mm |
| Tube IND | 30μ | 40μ | 40μ | 40μ | 40μ | 40μ | 40μ |
| Tube ID | 4 mm | 4.1 mm | 4.1 mm | 4.1 mm | 4.1 mm | 4.1 mm | 4.1 mm |
| Tube WT | 0.4 mm | 0.5 mm | 0.5 mm | 0.65 mm | 0.65 mm | 0.65 mm | 0.65 mm |
| Tube Porosity | 80.33% | 78.97% | 78.97% | 78.97% | 78.97% | 78.97% | 78.97% |
| Membrane Basis Weight | 8.426 gsm | 8.426 gsm | 8.426 gsm | 15.500 gsm | 15.500 gsm | 15.500 gsm | 15.500 gsm |
| Membrane Thickness | 40μ | 40μ | 40μ | 75μ | 75μ | 75μ | 75μ |
| Membrane Layers | 6 | 4 | 6 | 4 | 5 | 5 | 4 |
| Sintering Time | 4 min | 4 min | 5 min | 6 min | 6.5 min | 6.33 min | 8.33 min |
| Composite Thickness | 0.149 mm | 0.143 mm | 0.137 mm | 0.185 mm | 0.232 mm | 0.244 mm | 0.220 mm |

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

What is claimed is:

1. A process for forming a multilayered electrospun composite structure comprising:
    forming a dispersion of polymeric particles, a fiberizing polymer, and a solvent, the dispersion having a viscosity of at least about 50,000 cPs;
    electrospinning nanofibers from the dispersion onto a first expanded polytetrafluoroethylene layer;

applying a second expanded polytetrafluoroethylene layer onto the nanofibers to form a composite structure; and
heating the composite structure.

2. The process of claim 1, wherein the polymeric particles comprise polytetrafluoroethylene.

3. The process of claim 2, wherein the dispersion comprises about 50-80 weight percent of polytetrafluoroethylene.

4. The process of claim 2, wherein the dispersion comprises about 59-61 weight percent of polytetrafluoroethylene.

5. The process of claim 1, wherein the solvent comprises water.

6. The process of claim 1, wherein the fiberizing polymer comprises polyethylene oxide.

7. The process of claim 1, wherein the fiberizing polymer comprises a polyacrylamide, polyvinyl alcohol, polyvinylpyrrolidone, dextran, alginate, chitosan, guar gum compound, starch, cellulosic compound, polyacrylate, polycarboxylate, polylactic acid, polymethacrylic acid, or combinations thereof.

8. The process of claim 1, wherein the dispersion has a viscosity of at least about 100,000 cPs.

9. A process for forming a multilayered electrospun composite structure comprising:
electrospinning a dispersion having a viscosity of at least about 50,000 cPs and comprising polymeric particles, a fiberizing polymer, and a solvent, onto a first side of an expanded polytetrafluoroethylene layer;
electrospinning a dispersion having a viscosity of at least about 50,000 cPs and comprising polymeric particles, a fiberizing polymer, and a solvent, onto a second side of the expanded polytetrafluoroethylene layer to form a composite structure; and
heating the composite structure.

10. The process of claim 9, wherein at least a portion of the polymeric particles comprise polytetrafluoroethylene.

11. The process of claim 9, wherein the dispersion comprises about 59-61 weight percent of polytetrafluoroethylene.

12. The process of claim 9, further comprising sintering.

13. The process of claim 9, wherein the solvent comprises water.

14. A process for forming a multilayered electrospun composite structure comprising:
forming a dispersion of polymeric particles, a fiberizing polymer, and a solvent, the dispersion having a viscosity of at least about 50,000 cPs;
electrospinning nanofibers from the dispersion onto a first expanded polytetrafluoroethylene layer;
applying a substrate onto the nanofibers to form a composite structure; and
heating the composite structure.

15. The process of claim 14, wherein the polymeric particles comprise polytetrafluoroethylene.

16. The process of claim 15, wherein the dispersion comprises about 50-80 weight percent of polytetrafluoroethylene.

17. The process of claim 14, wherein the substrate comprises woven or nonwoven fabric.

18. The process of claim 14, wherein the substrate comprises a plastic or ceramic membrane.

19. The process of claim 14, wherein the substrate comprises a metal, ceramic, or plastic mesh.

20. A process for forming a multilayered electrospun composite structure comprising:
electrostatically spinning nanofibers from a dispersion onto a first expanded polytetrafluoroethylene layer, wherein the dispersion comprises polymeric particles, a fiberizing polymer, and a solvent and wherein the dispersion has a viscosity of at least about 50,000 cPs;
applying a second expanded polytetrafluoroethylene layer onto the nanofibers to form a composite structure; and
heating the composite structure.

21. A process for forming a multilayered electrospun composite structure comprising:
electrostatically spinning nanofibers from a dispersion onto a first expanded polytetrafluoroethylene layer, wherein the dispersion comprises polymeric particles, a fiberizing polymer, and a solvent, and wherein the dispersion has a viscosity of at least about 50,000 cPs;
applying a substrate onto the nanofibers to form a composite structure; and
heating the composite structure.

* * * * *